US008079361B2

(12) United States Patent
Schuler et al.

(10) Patent No.: US 8,079,361 B2
(45) Date of Patent: *Dec. 20, 2011

(54) INCREASED DOSAGE METERED DOSE INHALER

(75) Inventors: Carlos Schuler, Cupertino, CA (US); Andrew R. Clark, Woodside, CA (US); Kevin R. Walsh, San Francisco, CA (US); William Alston, San Jose, CA (US)

(73) Assignee: Novartis AG, Basel (CH)

( * ) Notice: Subject to any disclaimer, the term of this patent is extended or adjusted under 35 U.S.C. 154(b) by 197 days.

This patent is subject to a terminal disclaimer.

(21) Appl. No.: 12/337,584

(22) Filed: Dec. 17, 2008

(65) Prior Publication Data
US 2009/0095289 A1  Apr. 16, 2009

Related U.S. Application Data

(62) Division of application No. 10/698,025, filed on Oct. 30, 2003, now Pat. No. 7,481,212.

(60) Provisional application No. 60/422,563, filed on Oct. 30, 2002.

(51) Int. Cl.
*A61M 11/00* (2006.01)

(52) U.S. Cl. ................ 128/200.23; 128/200.14

(58) Field of Classification Search ............ 128/200.14, 128/200.23, 205.18, 205.24; 222/309, 310, 222/335, 341
See application file for complete search history.

(56) References Cited

U.S. PATENT DOCUMENTS

| 3,018,928 A | 1/1962 | Meshberg |
| 3,180,535 A | 4/1965 | Ward |
| 3,635,379 A | 1/1972 | Angele |
| 3,923,202 A | 12/1975 | Riccio |
| 4,413,755 A | 11/1983 | Brunet |
| 4,433,797 A * | 2/1984 | Galia ............................ 222/207 |
| 4,577,784 A | 3/1986 | Brunet |
| 4,819,834 A | 4/1989 | Thiel |
| 4,892,232 A | 1/1990 | Martin |
| 5,048,729 A | 9/1991 | Pritchard |
| 5,062,423 A | 11/1991 | Matson et al. |

(Continued)

FOREIGN PATENT DOCUMENTS

| GB | 1212373 | 11/1970 |
| WO | WO02/30498 | 4/2002 |

OTHER PUBLICATIONS

Dunbar, "Atomization Mechanisms of the Pressurized Metered Dose Inhaler", Particulat Sci. and Tech., 15:223-271, 1997.

(Continued)

*Primary Examiner* — Steven Douglas
(74) *Attorney, Agent, or Firm* — Janah & Associates, P.C.

(57) ABSTRACT

An aerosolization apparatus comprises a container containing a pharmaceutical formulation, the pharmaceutical formulation comprising an active agent and a propellant. The aerosolization apparatus further comprises a metering chamber in communication with the container, the metering chamber adapted to hold a metered amount of the pharmaceutical formulation, a valve to allow the metered amount of the pharmaceutical formulation to be released from the metering chamber when the valve is actuated, and a pressurizer that applies pressure to the pharmaceutical formulation in the metering chamber while the pharmaceutical formulation is being released from the metering chamber. In one version, the metering chamber is sized so that at least 2 mg, and preferably at least 5 mg, of the active agent is be aerosolized for delivery to a user during inhalation.

48 Claims, 12 Drawing Sheets

U.S. PATENT DOCUMENTS

| | | |
|---|---|---|
| 5,183,187 A | 2/1993 | Martin et al. |
| 5,357,946 A | 10/1994 | Kee et al. |
| 5,364,838 A | 11/1994 | Rubsamen |
| 5,366,115 A | 11/1994 | Kersten et al. |
| 5,662,271 A | 9/1997 | Weston et al. |
| 6,012,450 A | 1/2000 | Rubsamen |
| 6,260,549 B1 | 7/2001 | Sosiak |
| 6,341,603 B1 | 1/2002 | Howlett |
| 6,432,383 B1 | 8/2002 | Modi |
| 6,540,982 B1 | 4/2003 | Adjei et al. |
| 6,644,306 B1 * | 11/2003 | Riebe et al. .............. 128/200.23 |
| 7,481,212 B2 * | 1/2009 | Schuler et al. ........... 128/200.23 |

OTHER PUBLICATIONS

Dunbar et al., "An Experimental Investigation of the Spray Issued from a pMDI Using Laser Diagnostic Techniques", J. of Aerosol Med., vol. 10, No. 4, pp. 351-368, 1997.

Dunbar et al., "Theoretical Investigation of the Spray from a Pressurized Metered-Dose Inhaler", Atomization and Sprays, vol. 7, pp. 417-436, 1997.

Mohsen, "pMDI Aerosol Momentum Manipulation and Biotargeted Delivery", Respiratory Drug Delivery VIII, pp. 593-597, 2002.

* cited by examiner

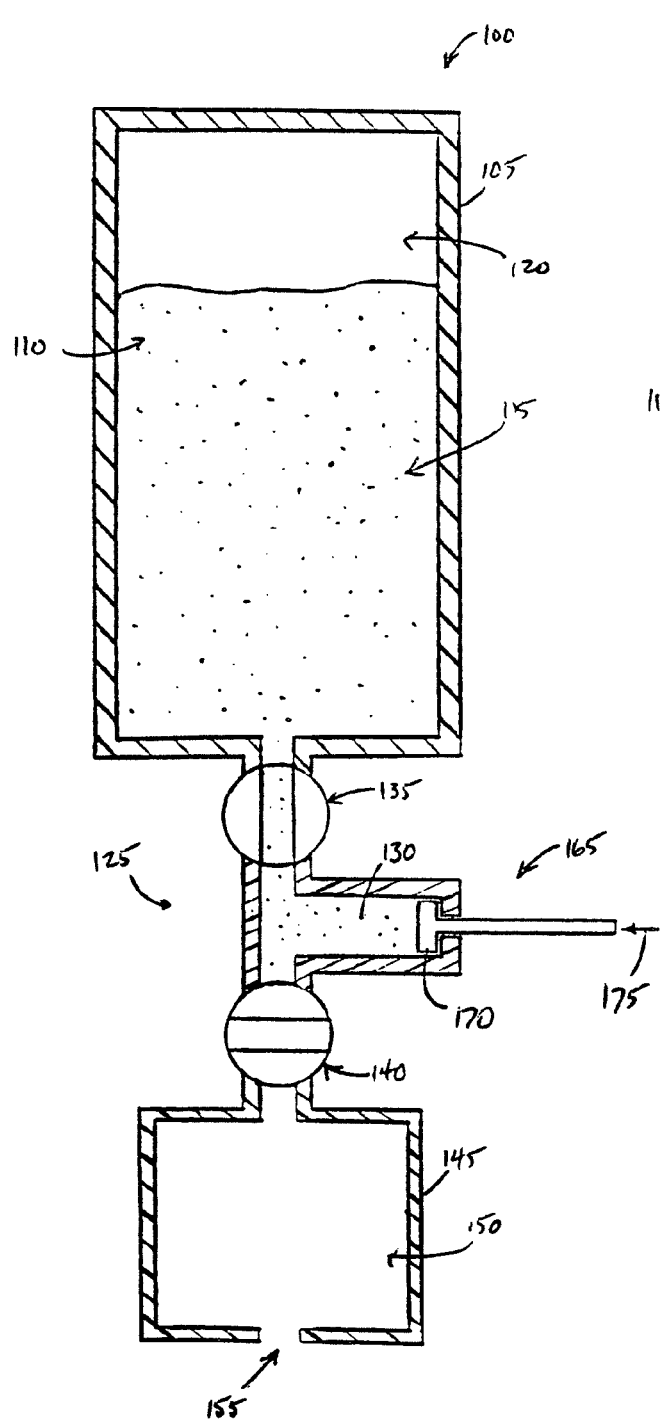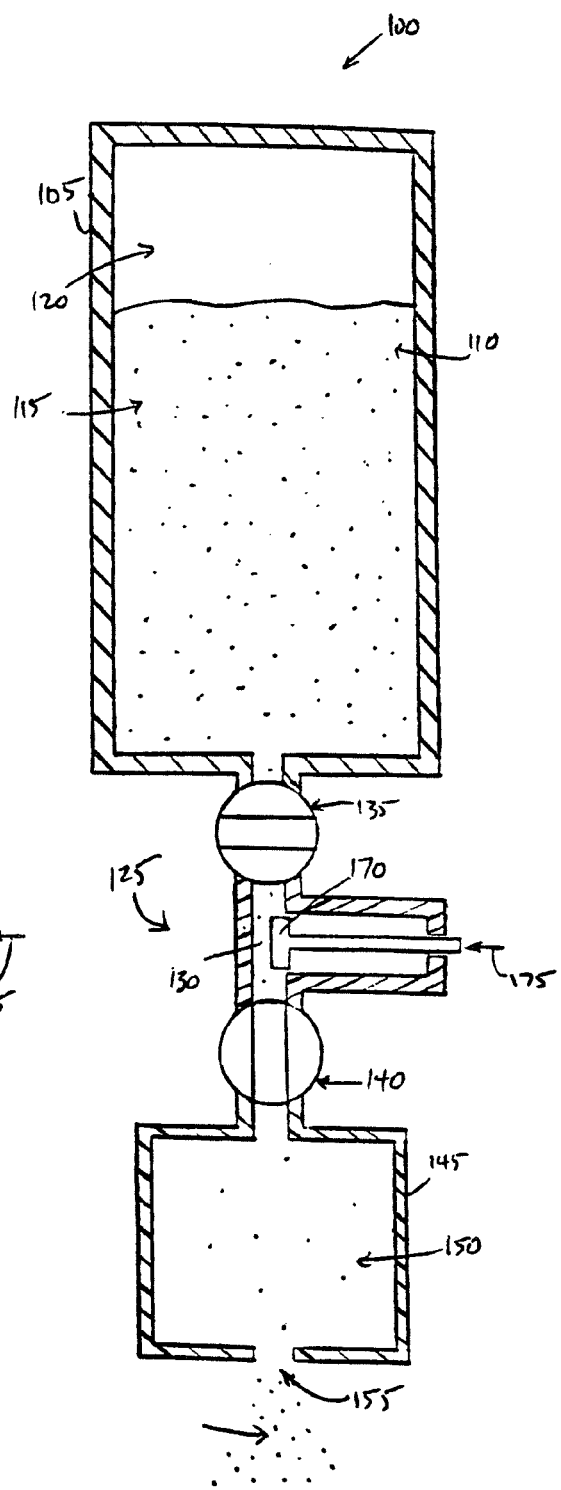
Figure 2A
Figure 2B

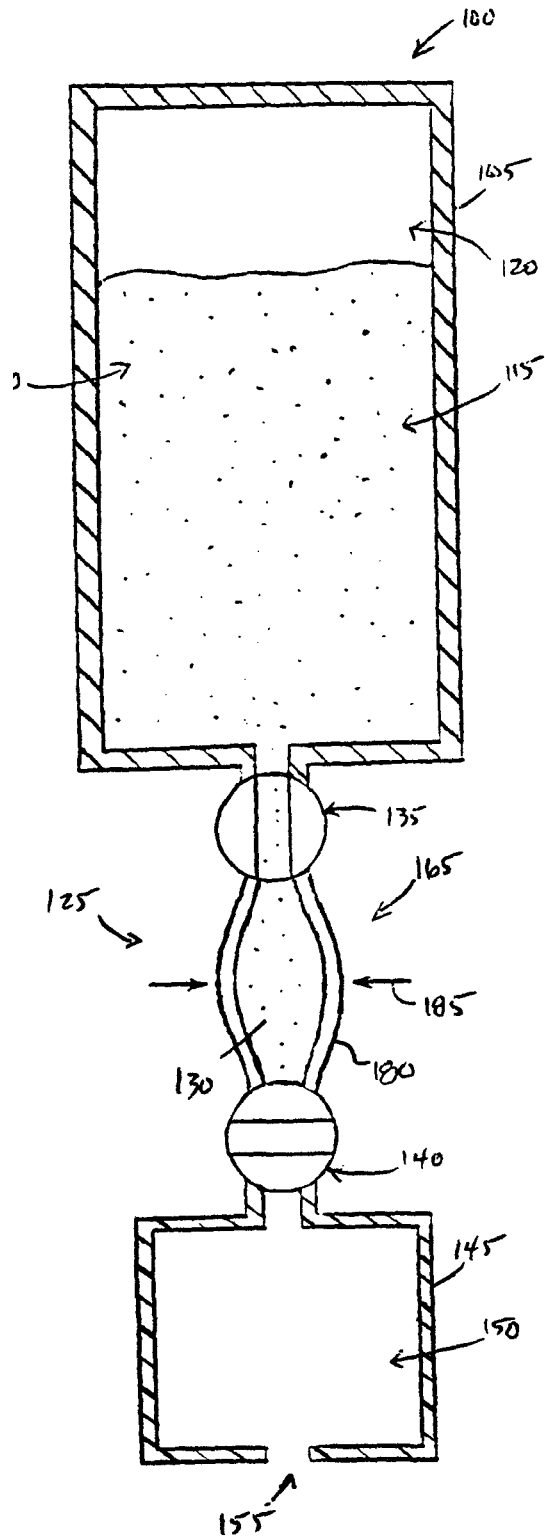
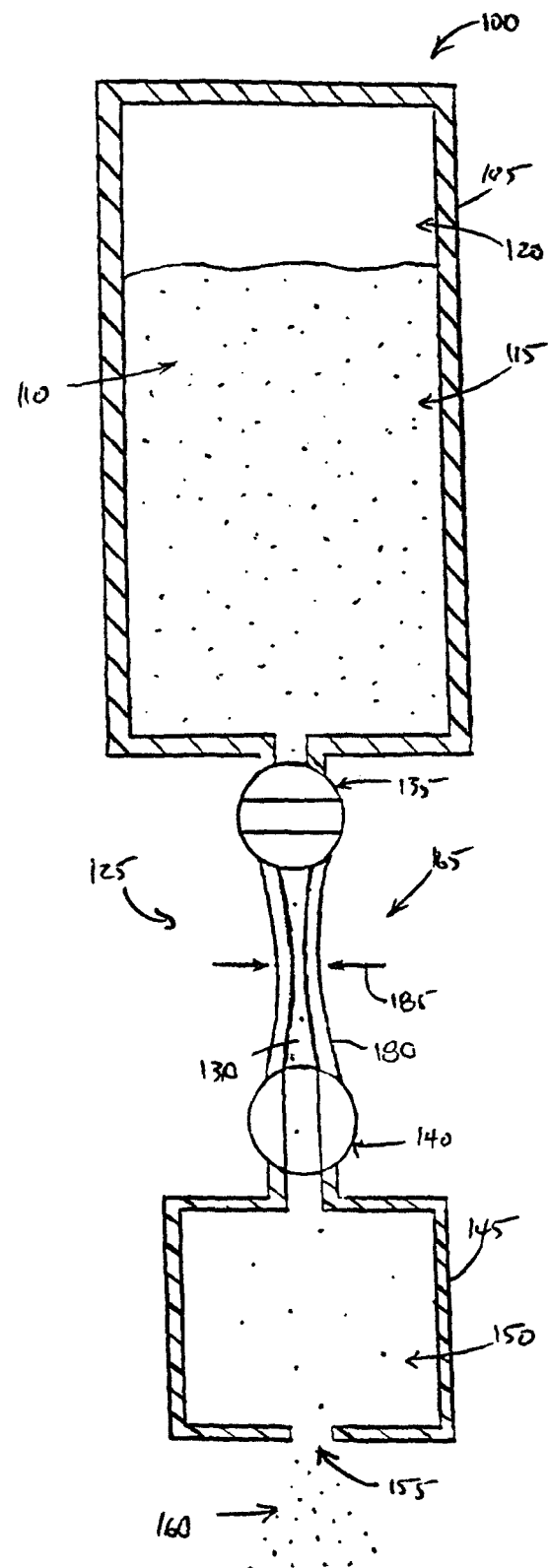
Figure 3A
Figure 3B

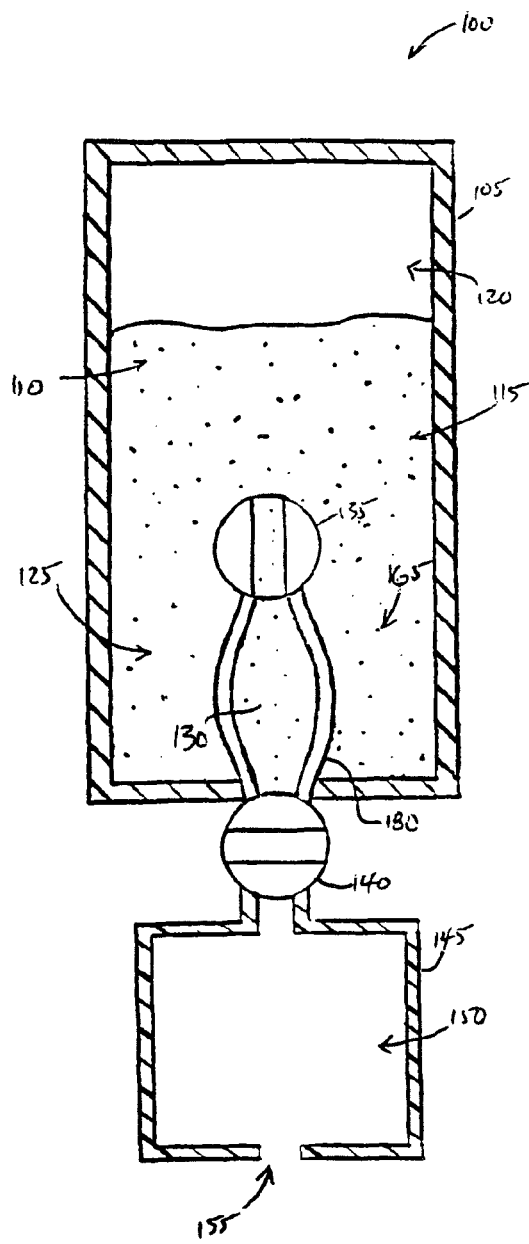
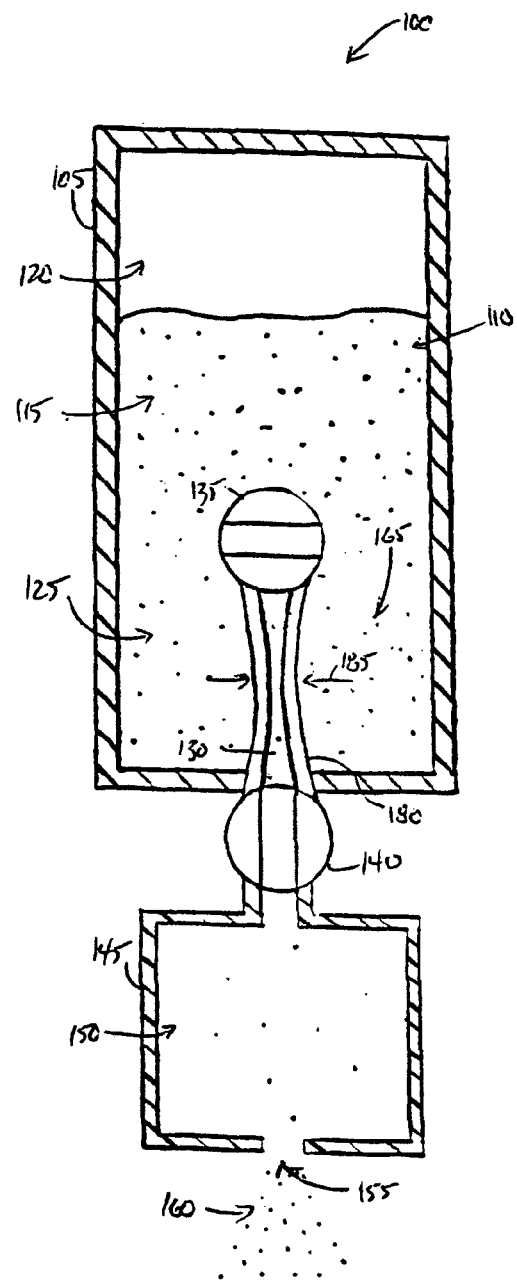
Figure 6A
Figure 6B

INCREASED DOSAGE METERED DOSE INHALER This application is a divisional of U.S. patent application Ser. No. 10/698,025, filed on Oct. 30, 2003, now U.S. Pat. No. 7,481,212, which claims the benefit of U.S. Provisional Patent Application Ser. No. 60/422,563, filed on Oct. 30, 2002, both of which are incorporated herein by reference in their entireties.

BACKGROUND

The need for effective therapeutic treatment of patients has resulted in the development of a variety of pharmaceutical formulation delivery techniques. One traditional technique involves the oral delivery of a pharmaceutical formulation in the form of a pill, capsule, elixir, or the like. However, oral delivery can in some cases be undesirable. For example, many pharmaceutical formulations may be degraded in the digestive tract before they can be effectively absorbed by the body. Inhalable drug delivery, where an aerosolized pharmaceutical formulation is orally or nasally inhaled by a patient to deliver the formulation to the patient's respiratory tract, has proven to be a particularly effective and/or desirable alternative. For example, in one inhalation technique, an aerosolized pharmaceutical formulation provides local therapeutic relief to a portion of the respiratory tract, such as the lungs, to treat diseases such as asthma and emphysema. In another inhalation technique, a pharmaceutical formulation is delivered deep within a patient's lungs where it may be absorbed into the blood stream. Many types of aerosolization devices exist including devices comprising a pharmaceutical formulation stored in or with a propellant, devices that aerosolize a dry powder, devices which use a compressed gas to aerosolize a liquid pharmaceutical formulation, and similar devices.

One conventional type of aerosolization device is commonly referred to as a metered dose inhaler (MDI), which is sometimes referred to as a pressurized metered dose inhaler (pMDI). In a metered dose inhaler, a pharmaceutical formulation and a propellant are stored in a canister. In one version the pharmaceutical formulation is suspended within the propellant, and in another version the pharmaceutical formulation is dissolved in the propellant. In either version, a valve may be actuated so that a metered amount, or dose, of the pharmaceutical formulation is aerosolized in a manner where is may be inhaled by a user. The canister may contain one or more doses of the pharmaceutical formulation and generally contains sufficient amounts of propellant to allow for several actuations. Traditionally, the propellant comprises one or more chlorofluorocarbon compounds. However, non-chlorinated propellants, such as hydrofluoroalkanes, that are believed to be more environmentally friendly are proving to be a desirable alternative.

Though generally well accepted and inexpensive, metered does inhalers have certain drawbacks. For example, the amount of pharmaceutical formulation that may be aerosolized during an actuation is limited. In addition, it can often be difficult to control the efficiency of delivering large quantities of a pharmaceutical formulation using a metered dose inhaler.

Therefore, it is desirable to be able to aerosolize a pharmaceutical formulation in an efficient manner. It is further desirable to provide an improved metered dose inhaler that is capable of effectively aerosolizing a large quantity of a pharmaceutical formulation. It is still further desirable to provide an improved metered dose inhaler with improved aerosolization efficiency and reproducibility.

SUMMARY

The present invention satisfies these needs. In one aspect of the invention a large and/or uniform aerosol dose of medicament is delivered from a metered dose inhaler.

In another aspect of the invention, an aerosolization apparatus comprises a container containing a pharmaceutical formulation, the pharmaceutical formulation comprising an active agent and a propellant; a metering chamber in communication with the container, the metering chamber adapted to hold a metered amount of the pharmaceutical formulation; a valve to allow the metered amount of the pharmaceutical formulation to be released from the metering chamber when the valve is actuated; and a pressurizer that applies pressure to the pharmaceutical formulation in the metering chamber while the pharmaceutical formulation is being released from the metering chamber, wherein the metering chamber is sized so that at least 2 mg of the active agent is be aerosolized for delivery to a user during inhalation.

In another aspect of the invention, an aerosolization apparatus comprises a container containing a pharmaceutical formulation, the pharmaceutical formulation comprising an active agent and a propellant; a metering chamber in communication with the container, the metering chamber having a metering volume of at least 150 µl and being adapted to hold a metered amount of the pharmaceutical formulation; a valve to allow the metered amount of the pharmaceutical formulation to be released from the metering chamber when the valve is actuated; and a pressurizer that applies pressure to the pharmaceutical formulation in the metering chamber while the pharmaceutical formulation is being released from the metering chamber.

In another aspect of the invention, an aerosolization apparatus comprises a container containing a pharmaceutical formulation, the pharmaceutical formulation comprising insulin and a propellant; a metering chamber in communication with the container, the metering chamber adapted to hold a metered amount of the pharmaceutical formulation; a valve to allow the metered amount of the pharmaceutical formulation to be released from the container when the valve is actuated; and a pressurizer that applies pressure to the pharmaceutical formulation in the metering chamber while the pharmaceutical formulation is released from the metering chamber.

In another aspect of the invention, a method of aerosolizing a pharmaceutical formulation comprises containing a pharmaceutical formulation in a container, the pharmaceutical formulation comprising an active agent and a propellant; metering an amount of the pharmaceutical formulation in a metering chamber in communication with the container; releasing the pharmaceutical formulation from the metering chamber when a valve is actuated; and applying pressure within the metering chamber during the release of the pharmaceutical formulation, wherein at least 2 mg of the active agent is be aerosolized for delivery to a user during inhalation.

In another aspect of the invention, a method of aerosolizing an insulin formulation comprises containing a pharmaceutical formulation in a container, the pharmaceutical formulation comprising insulin and a propellant; metering an amount of the pharmaceutical formulation in a metering chamber in communication with the container; releasing the pharmaceutical formulation from the metering chamber when a valve is actuated; and applying pressure within the metering chamber during the release of the pharmaceutical formulation.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

FIGS. 2A and 2B are schematic sectional side views of a version of an aerosolization device of the invention;

FIGS. 3A and 3B are schematic sectional side views of another version of an aerosolization device of the invention;

FIGS. 6A and 6B are schematic sectional side views of a version of an aerosolization device of the invention in accordance with the version of FIGS. 3A and 3B;

DESCRIPTION

The present invention relates to an aerosolization device, such as a device that uses a propellant for aerosolization, and its method of use. Although the process is illustrated in the context of aerosolizing a predetermined amount of a pharmaceutical formulation, the present invention can be used in other processes and should not be limited to the examples provided herein.

Figure 1A:
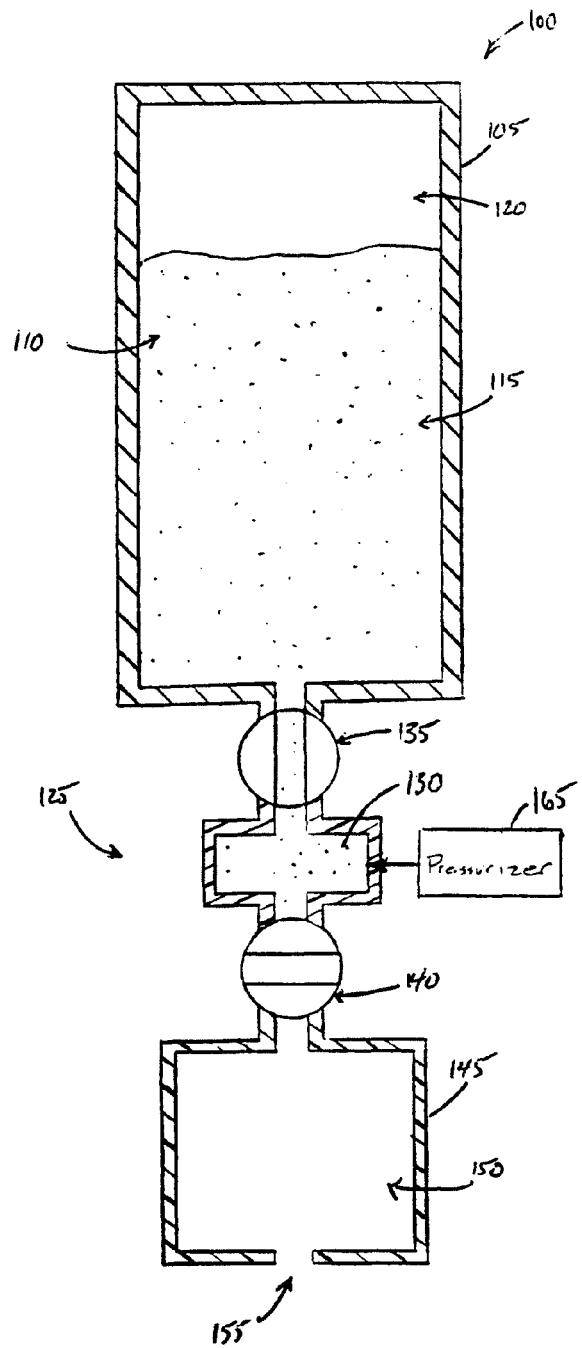
FIGS. 1A and 1B are schematic sectional side views of an aerosolization device of the invention.

An aerosolization device 100 of the present invention is shown schematically in FIG. 1A. A container 105 includes a reservoir 110 which stores a formulation, such as a pharmaceutical formulation, comprising a propellant. The formulation may further comprise an active agent dissolved in or suspended in the propellant or a mixture comprising the propellant. The propellant may comprise a superheated liquid that may be used as an atomizing energy source during actuation of the aerosolization device 100. As shown in FIG. 1A, the pharmaceutical formulation within the container 105 may include a liquid portion 115 and a gaseous portion 120 also known as a headspace.

Figure 1B:
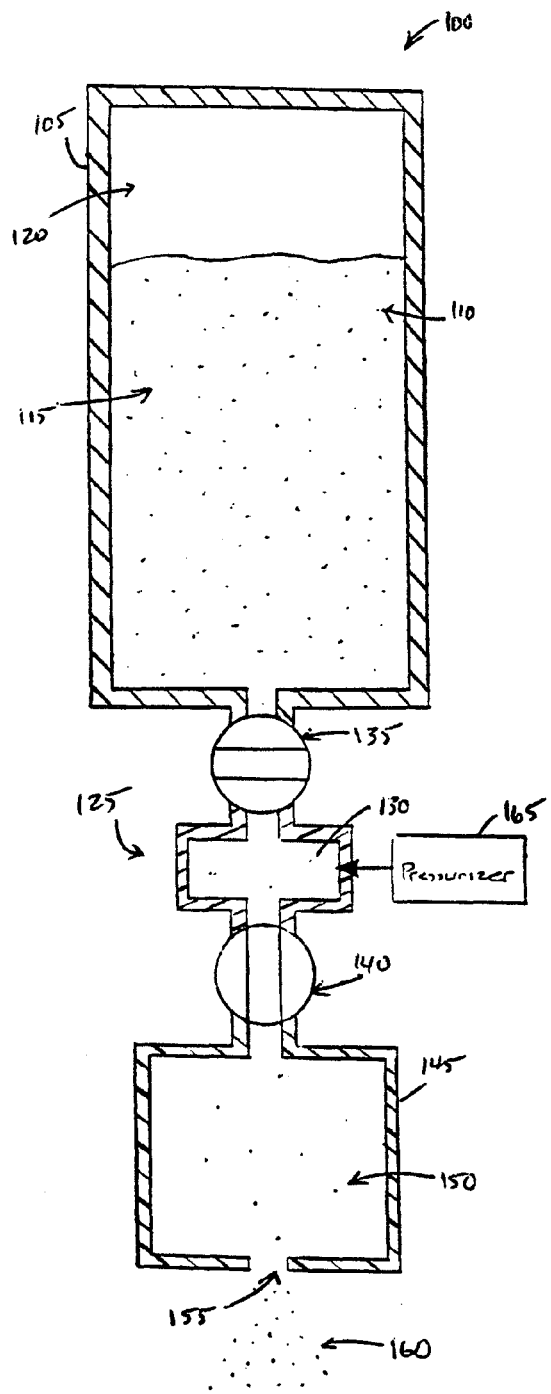

In communication with the reservoir 110 is a metering valve 125 that is capable of allowing a metered amount of the pharmaceutical formulation to be released from the reservoir 110 in an aerosolized form. The operation of the metering valve 125 is shown in FIGS. 1A and 1B. The metering valve 125 comprises a metering chamber 130 sized to contain a predetermined amount of the pharmaceutical formulation. A first valving mechanism 135 is moveable between an open position and a closed position. In the open position, as shown in FIG. 1A, the metering chamber 130 is in communication with the reservoir 110 in the container 105 so that the pharmaceutical formulation in the reservoir 110 may flow into the metering chamber 130. In the closed position, as shown in FIG. 1B, the pharmaceutical formulation in the reservoir 130 does not flow into the metering chamber 130. A second valving mechanism 140 is moveable between an open position, as shown in FIG. 1B, and a closed position, as shown in FIG. 1A. When the second valving mechanism 140 is opened, the metered amount of the pharmaceutical formulation in the metering chamber 130 is allowed to flow out of the metering chamber 130 and into an expansion chamber 145.

The metered amount of the pharmaceutical formulation is ejected from the metering chamber 130 into the interior 150 of the expansion chamber 145 under the pressure of the flashing liquid propellant. As the propellant boils, vapor is generated to fill the void left in the metering chamber 130. In the expansion chamber 145 the pharmaceutical formulation undergoes expansion and further boiling. As a result, the metered amount of pharmaceutical formulation is discharged through a spray orifice 155 as an aerosolized pharmaceutical formulation 160.

In one version of the present invention, a pressurizer 165 provides additional pressure to the pharmaceutical formulation in the metering chamber 130 and/or the expansion chamber 145 during the aerosolization process. As the pharmaceutical formulation is released from the metering chamber 130, the quantity of propellant in the metering chamber 130 decreases and the pressure generated from the boiling propellant decreases. In addition, as the propellant exits the metering chamber 130, the expansion required to continuously fill the volume causes the propellant to cool which results in lower vapor pressures. The pressure generated from the propellant eventually becomes too low to effectively drive the pharmaceutical formulation out of the expansion chamber 145 and through the orifice 160. The pressurizer 165 provides additional pressure to compensate for this loss of pressure.

The added pressure from the pressurizer 165 allows for improved aerosolization of the pharmaceutical formulation. For example, in one version, the added pressure allows for a larger quantity of the pharmaceutical formulation to be aerosolized as a metered amount. Without the added pressure, the amount of pharmaceutical formulation that may be aerosolized is limited due to the dissipating energy from the reduced vapor pressure. However, with the added pressure from the pressurizer 165, the amount of pharmaceutical formulation that may be aerosolized is unlimited. Accordingly, in one version, the aerosolization device 100 aerosolizes more than about 2 mg, preferably more than about 3 mg, and more preferably more than about 5 mg of the pharmaceutical formulation. In addition, without the added pressure, aerosolized particle size distribution for even low quantity metered amounts may be unacceptably high. However, with the aerosolization device 100, the added pressure from the pressurizer 165 allows for small quantities of the pharmaceutical formulation to be more effectively aerosolized. For example, in one version, the aerosolization device 100 may aerosolize a metered amount containing more than about 0.5 mg of the pharmaceutical formulation with the aerosolized particle size distribution being acceptably low. The size of the metering chamber 130 and the amount of the pharmaceutical formulation delivered are limited only by the geometry of the device and the inhalation capabilities of a user. In one version, the volume of the metering chamber 130 may be at least about 50 µl, preferably at least about 150 µl, and more preferably at least about 300 µl, and most preferably about 360 µl. In one particular version, at least 50% of the aerosol particles generated have a diametric size of from 0.1 µm to 10 µm, more preferably from 1 µm to 5 µm. Even more preferably at least about 80% of the aerosolized particles are within the desired size ranges.

In one version, the pressurizer 165 may comprise a mechanism that changes the volume of the metering chamber 130. Since pressure is related to volume, by decreasing the volume of the metering chamber 130, the pressure in the chamber is increased. For example, as shown in FIGS. 2A and 2B, the pressurizer 165 comprises a moveable member, such as a plunger 170. A force 175 may be applied to the plunger during the aerosolization process so that the pressure in the metering chamber 130 does not dissipate as rapidly as it would in a constant volume metering chamber. The force 175 may be constant or may vary. In one version, the force 175 is constant and substantially equal to the force acting on the plunger 170 by the pressurized gas in the filling position of FIG. 2A so that a substantially constant pressure is applied for at least a period of time during the aerosolization process of FIG. 2B. In another version, the force 175 is slightly less than the force acting on the plunger 170 by the pressurized pharmaceutical formulation in the filling position of FIG. 2A. In this version, when in the filling position of FIG. 2A, the force acting on the plunger 170 from the pressurized pharmaceutical formulation is sufficient to move the plunger 170 to the retracted position shown in FIG. 2A.

Alternatively or additionally, the pressurizer 165 may change the volume of the metering chamber 130 by providing the metering chamber 130 with one or more flexible walls 180, as shown for example in FIGS. 3A and 3B. For example, the flexible wall 180 may be composed of a flexible polymeric or natural material. A force 185 may act on the wall 180 to cause the wall 180 to collapse and thereby decrease the volume of the metering chamber 130. The magnitude of the force 185 may be similar to that discussed above in connection with FIGS. 2A and 2B. In one version, the wall 180 may be biased into the position shown in FIG. 3A to allow the metering chamber 130 to be filled with the metered amount of pharmaceutical formulation during the filling process. In another version, the pressure of the pharmaceutical formulation may be greater than the force 185 to cause the wall 180 to expand to configuration shown in FIG. 3A. During the aerosolization process shown in FIG. 3B, the force 185 causes the metering chamber 130 to decrease in volume to add pressure to the metering chamber 130.

Figures 4A, 4B:
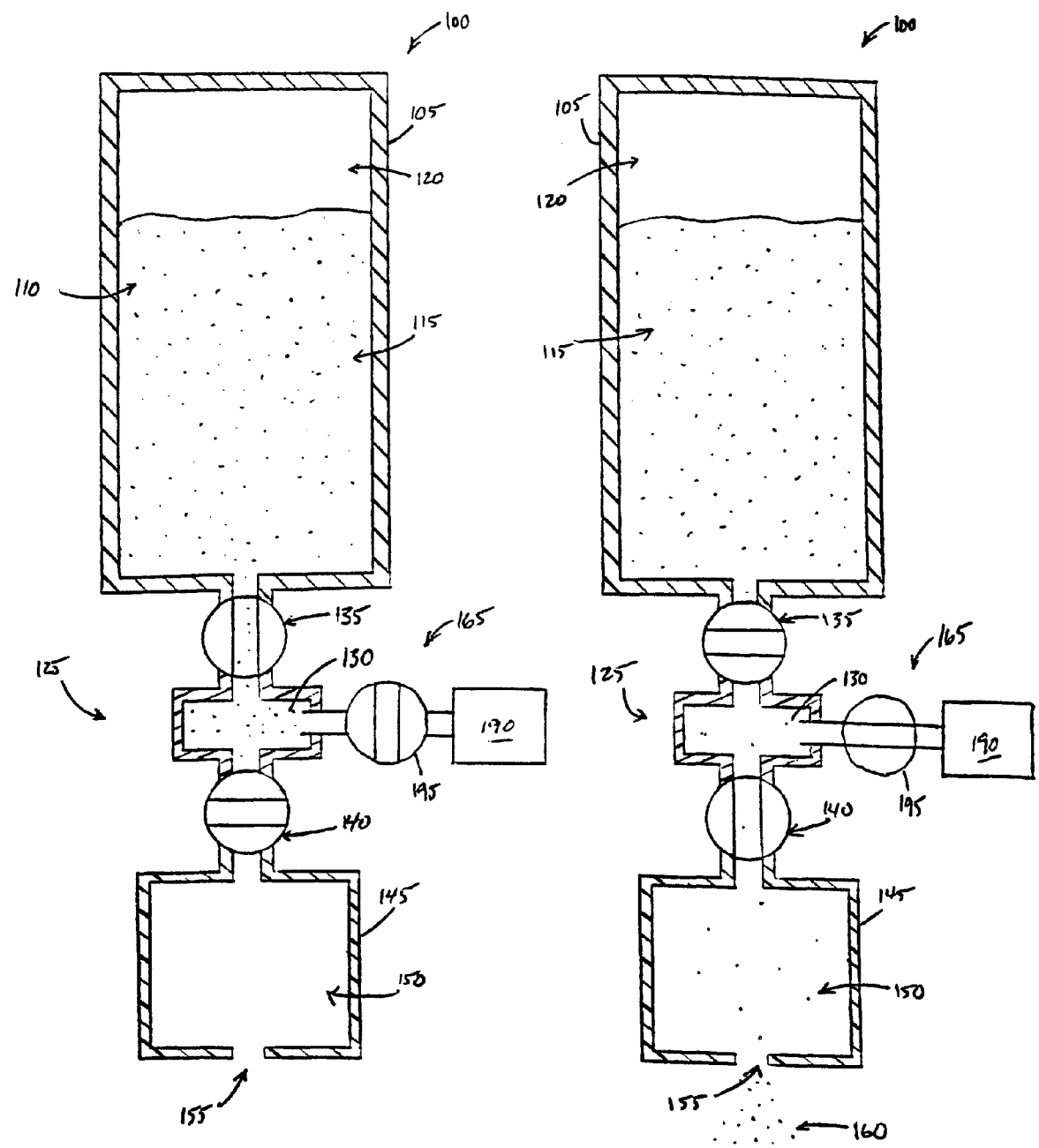
FIGS. 4A and 4B are schematic sectional side views of another version of an aerosolization device of the invention.

In another version, the pressurizer 165 uses pressurized gas to add pressure to the metering chamber 130. For example, as shown in the version of FIGS. 4A and 4B, the pressurizer 165 may comprise a source of pressurized gas 190 that is capable of communicating with the metering chamber 130. A third valving mechanism 195 is provided to control the application of the pressurized gas to the metering chamber 130. During the metering chamber filling process of FIG. 4A, the third valving mechanism 195 is closed to allow the metering chamber 130 to fill with the pharmaceutical formulation from the reservoir 110 in the container 105. During the aerosolization process shown in FIG. 4B, the third valving mechanism 195 is opened to allow the pressurized gas to flow into the metering chamber 130 to increase the pressure therein. In one version, the third valving mechanism 195 is returned to the closed position after a period of time to prevent excessive loss of the pressurized gas through the orifice 155. Accordingly, in this version the pressurizer 165 provides a burst of pressurized gas to the metering chamber 130 when the pharmaceutical formulation is being emptied from the metering chamber 130.

In particularly useful versions of the present invention, the metering valve 125 may be at least partially within the container 105. When the metering valve 125 is provided at least partially in the container 105, the pressurized pharmaceutical formulation may be used to supply the energy for the pressurizer 165. Thus, the need for an addition force applicator or source of pressurized gas is eliminated.

Figure 5A:
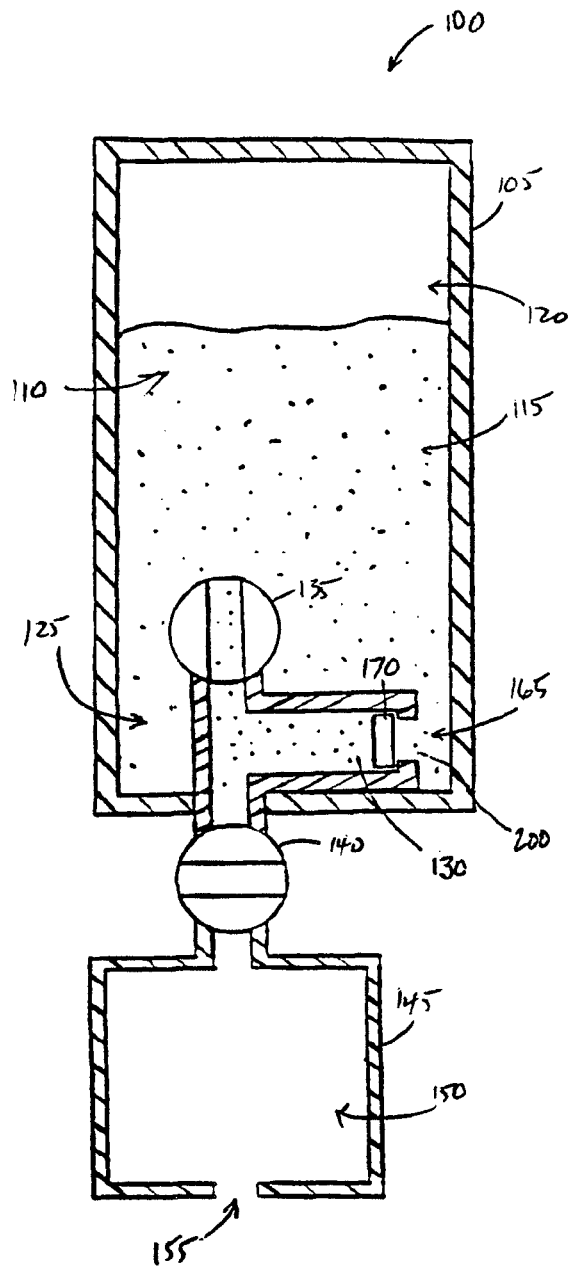
FIGS. 5A and 5B are schematic sectional side views of a version of an aerosolization device of the invention in accordance with the version of FIGS. 2A and 2B.
Figure 5B:
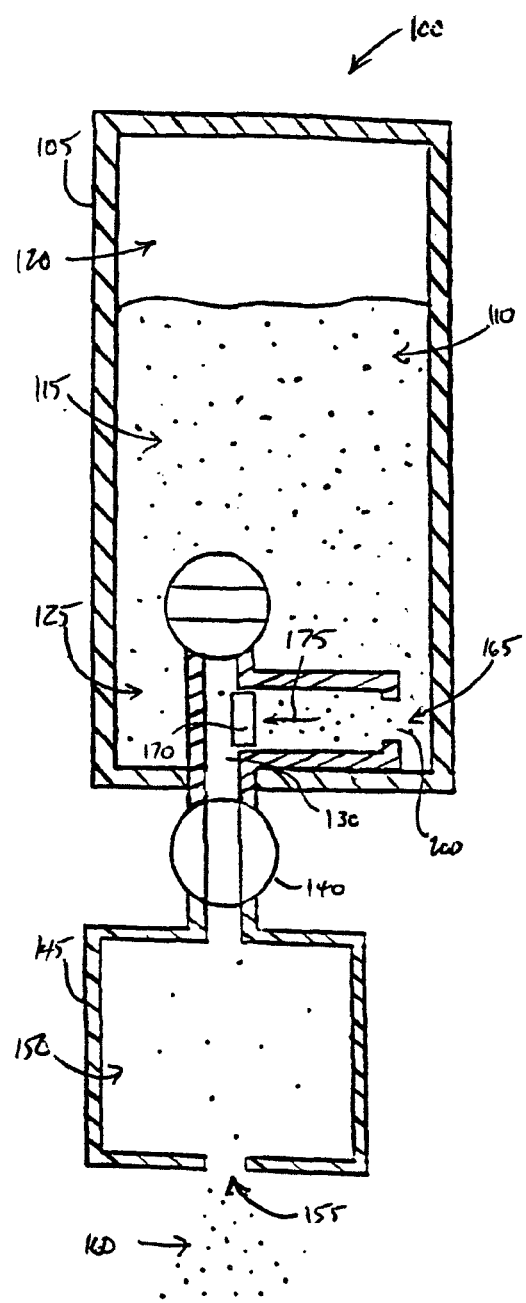

FIGS. 5A and 5B show a version of an aerosolization device 100 similar to the version of FIGS. 2A and 2B, but with at least a portion of the metering valve 125 being within the container 105. In this version, the pressurizer 165 comprises a plunger 170 that is moveable within the metering chamber 130 to reduce the volume of the metering chamber 130 during pharmaceutical formulation aerosolization. In the filling position shown in FIG. 5A, the pharmaceutical formulation is allowed to flow from the reservoir 110 into the metering chamber 130. The plunger 170 separates the metering chamber 130 from the reservoir 110. One side of the plunger 170 is acted on by the pressure within the metering chamber 130 and another side of the plunger 170 is acted on by the pressure within the reservoir. In the FIG. 5A condition, the first valving mechanism 135 is open and there is equilibrium between the metering chamber 130 and the reservoir 110. Accordingly, the plunger 170 does not move. When the aerosolization device 100 is actuated to cause the metered amount of the pharmaceutical formulation to be aerosolized, as shown in FIG. 5B, the pressure within the metering chamber 130 begins to decrease, as discussed above. As a result, the pressure from the reservoir 110 is greater than the pressure from the metering chamber 130 and the plunger 170 is caused to move as shown to reduce the volume of the metering chamber 130 and to reduce the decrease in pressure in the metering chamber 130. A biasing member, such as a spring (not shown) may also be provided to return the plunger to the retracted position shown in FIG. 5A when the aerosolization process is completed and the metering chamber 130 is to be filled again.

In like manner, the version of FIGS. 6A and 6B are similar to the version of FIGS. 3A and 3B with at least a portion of the metering valve 125 being within the container 105. In this version, the pressurizer 165 comprises a flexible wall 180 on the metering chamber 130, and the pressurized pharmaceutical formulation within the reservoir 110 acts on the flexible wall 180 of the metering chamber 130 to cause the metering chamber 130 to have a reduced volume during the aerosolization process, as shown in FIG. 6B. The flexible wall 180 may be biased into its expanded position shown in FIG. 6A to allow the metered amount of the pharmaceutical to enter into the metering chamber 130. Upon actuation and during aerosolization, as shown in FIG. 6B, the pressure in the reservoir 110 is greater than the pressure in the metering chamber 130 and the wall 180 of the metering chamber moves so as to reduce the volume in the metering chamber 130.

Figure 7A:
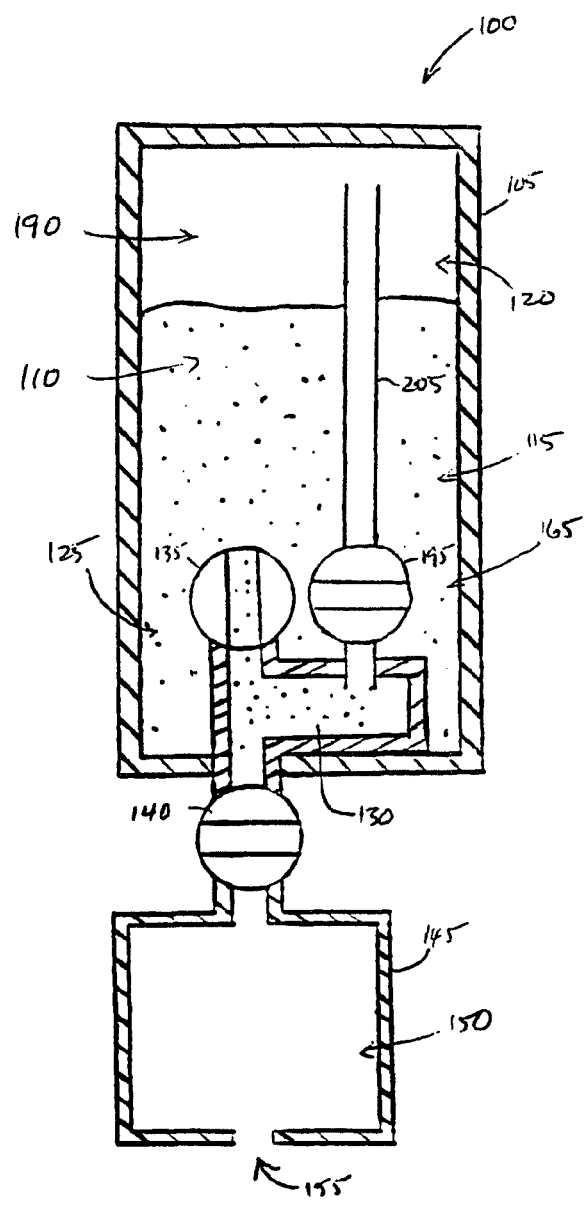
FIGS. 7A and 7B are schematic sectional side views of a version of an aerosolization device of the invention in accordance with the version of FIGS. 4A and 4B.
Figure 7B:
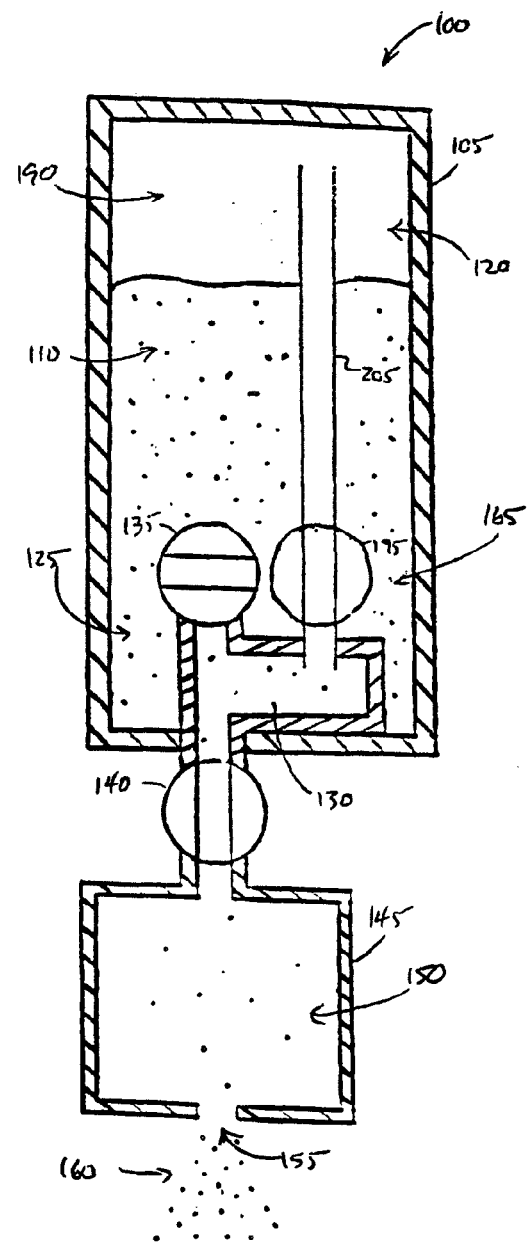

In the version of FIGS. 7A and 7B, the pressurizer 165 comprises an arrangement that allows pressurized gas to be introduced into the metering chamber during the aerosolization process, as in the version of FIGS. 4A and 4B. However, in the version of FIGS. 7A and 7B, the source of pressurized gas 190 is the gaseous component 120 in the reservoir 110 of the container 105. The pressurizer 165 in this version comprises a conduit 205 that extends into the gaseous portion 120 and which allows the gaseous portion 120 to communicate with the metering chamber 130 when the third valving mechanism 195 is open.

Figure 8:
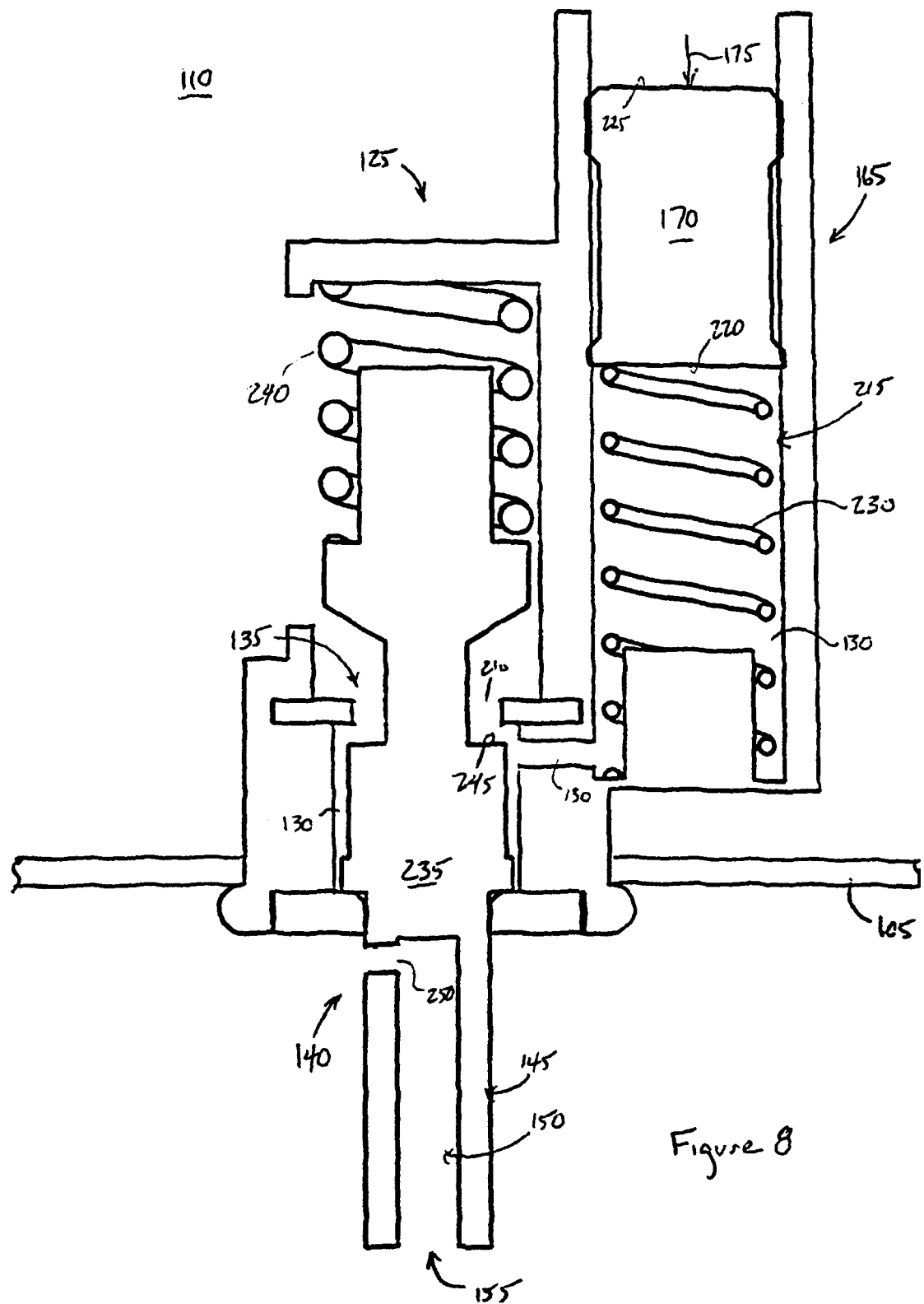
FIG. 8 is a schematic sectional side view of a specific version of an aerosolization device in accordance with the version of FIGS. 5A and 5B.
Figure 9:
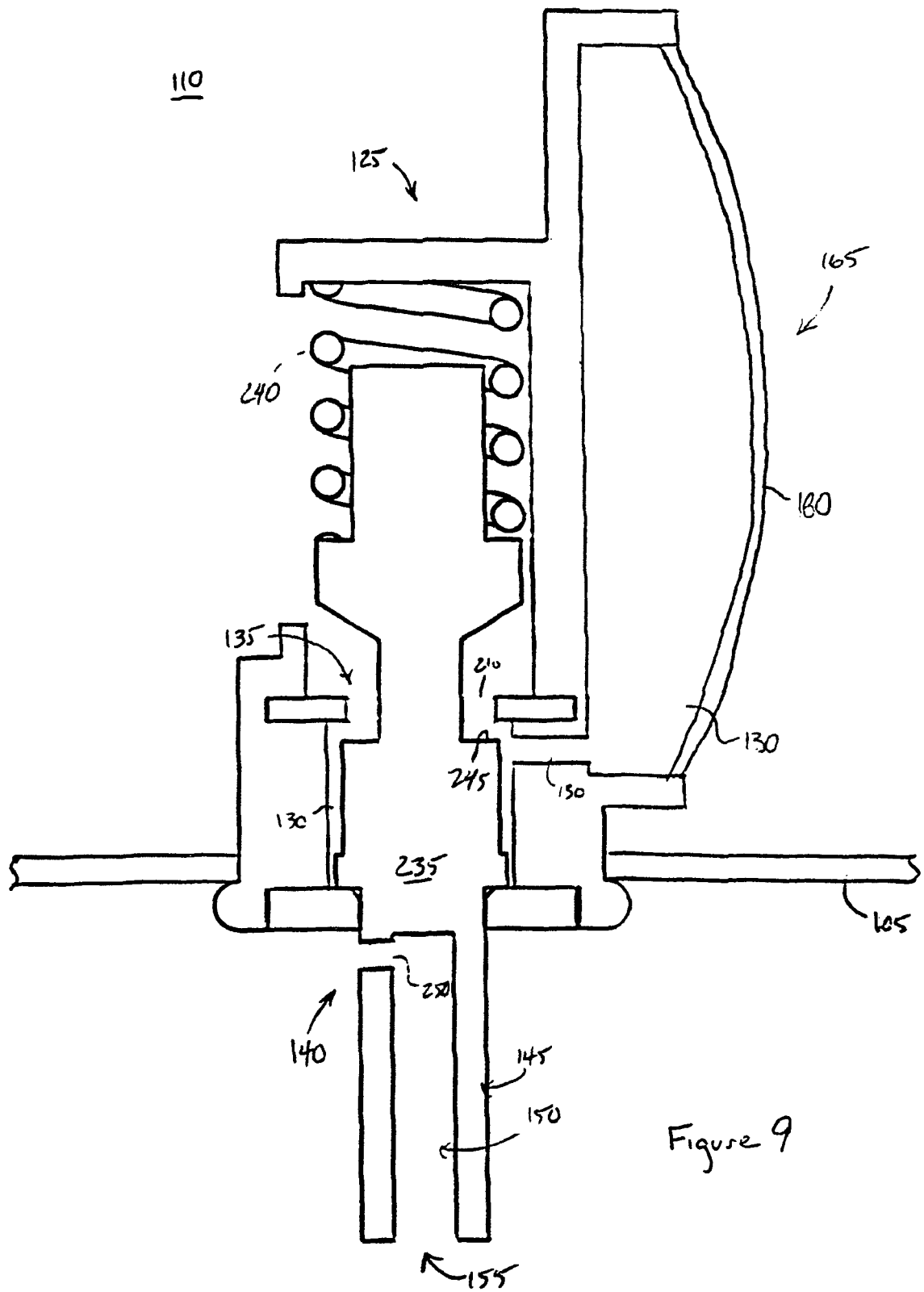
FIG. 9 is a schematic sectional side view of a specific version of an aerosolization device in accordance with the version of FIGS. 6A and 6B.
Figure 10:
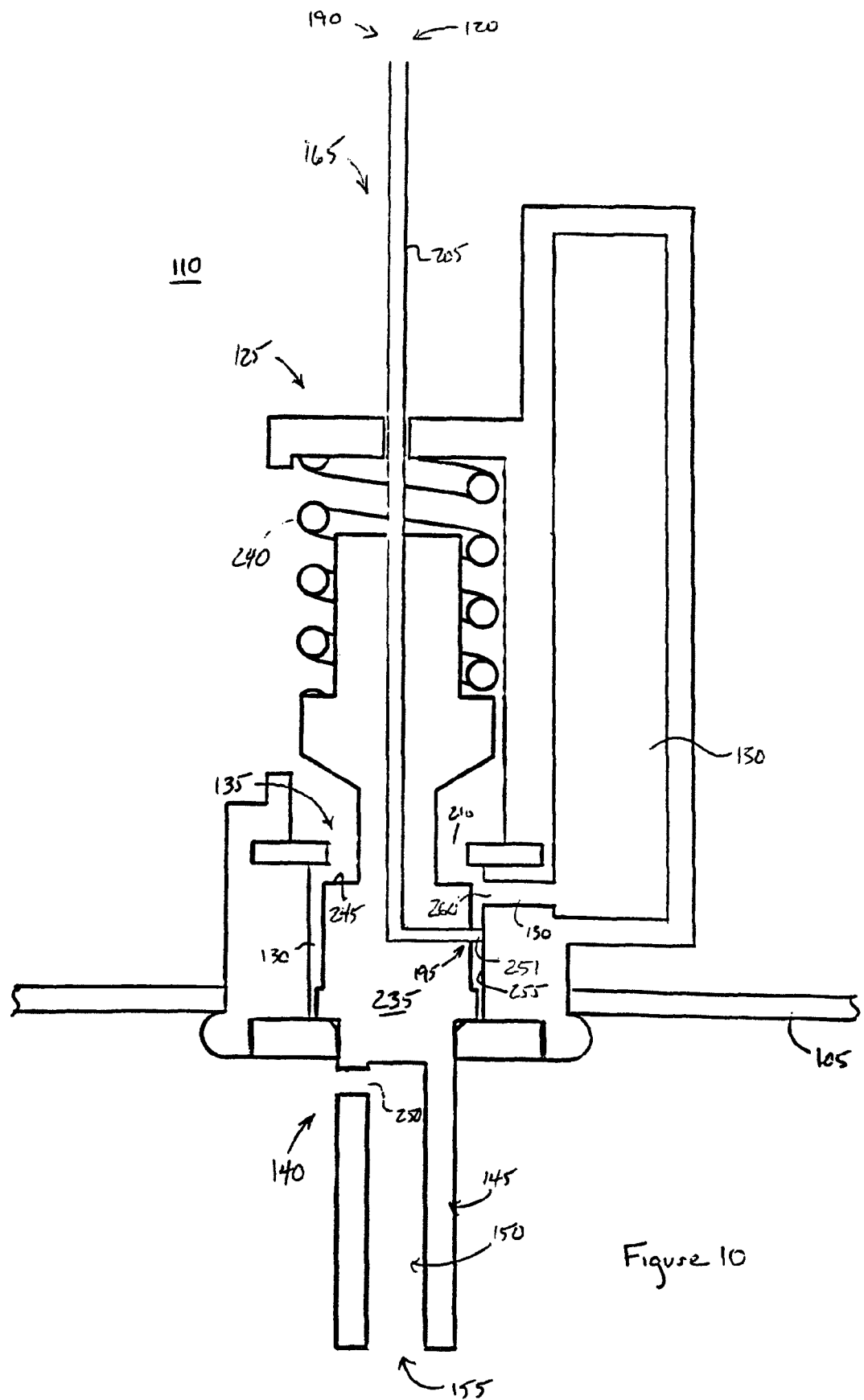
FIG. 10 is a schematic sectional side view of a specific version of an aerosolization device in accordance with the version of FIGS. 7A and 7B.
Figure 11:
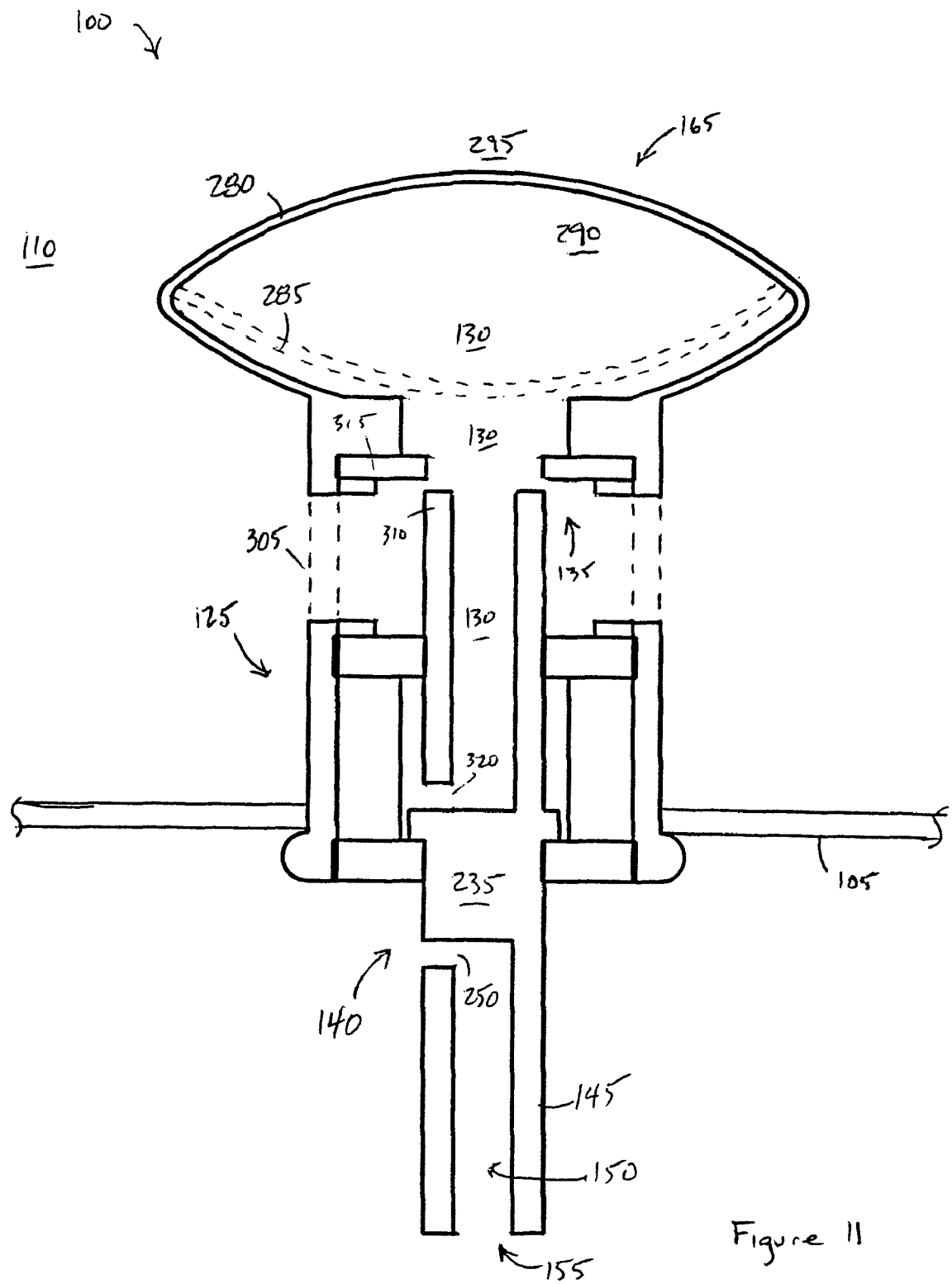
FIG. 11 is a schematic sectional side view of another specific version of an aerosolization device of the invention.
Figure 12:
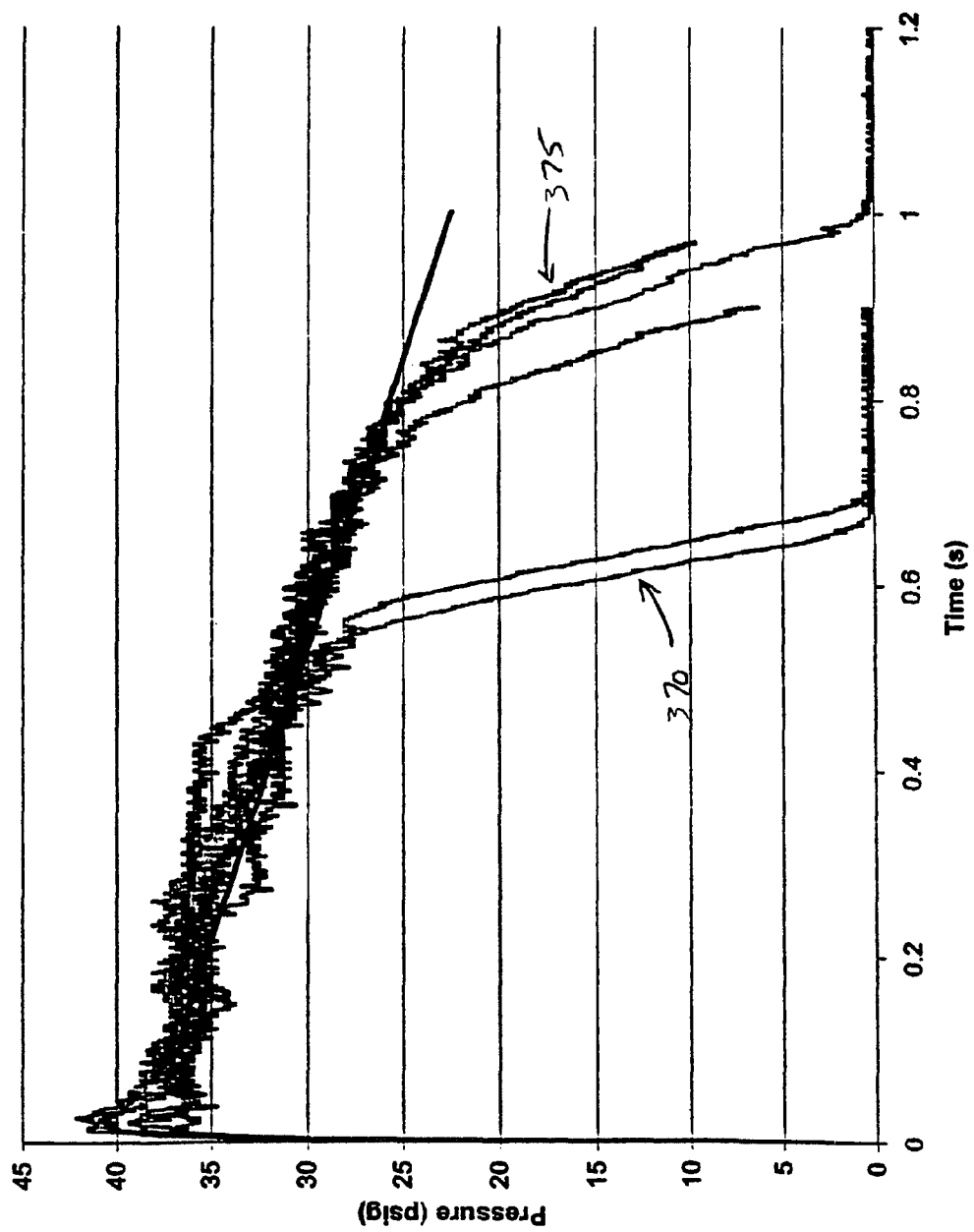
FIG. 12 is a graph showing data obtained from experiments performed with the version of the aerosolization device shown in FIG. 8.

FIG. 8 shows a specific version of a metering valve 125 comprising a pressurizer 165. The metering valve 125 is positioned within the reservoir 110 of a container 105 containing a pharmaceutical formulation comprising a propellant. FIG. 8 shows the metering valve 125 in its filling position. The pharmaceutical formulation flows through an opening into the metering chamber 130. In a portion 215 of the metering chamber 130 a plunger is moveably positioned. One side 220 of the plunger is acted on by the pressure in the metering chamber 130. Another side 225 of the plunger is acted on by pressure in the reservoir 110. When in the filling position, the first valving mechanism 135 is open and the pressure in the metering chamber 130 is the same as the pressure in the reservoir 110. A biasing member 230 biases the plunger 170 to the position shown in FIG. 8. The metering valve 125 comprises a moveable stem 235. The stem 235 is biased into the position shown in FIG. 8 by a spring 240. Movement of the stem 235 to compress the spring 240 causes actuation of the aerosolization device 100 which results in aerosolization of the pharmaceutical formulation contained within the metering chamber 130. This movement of the stem 235 causes the first valving mechanism 135 to close by causing a portion 245 of the stem to block the opening 210 into the metering chamber 130. Simultaneously or shortly thereafter upon continued movement of the stem 235, the second valving member 140 is opened by causing an opening 250 into the interior 150 of the expansion chamber 145 to be in communication with the metering chamber 130. The pharmaceutical formulation in the metering chamber 130 is them ejected into the expansion chamber 145, as discussed above. As the pressure in the metering chamber 130 is reduced, the pressure difference on the plunger 170 becomes sufficiently large to overcome the force of the biasing member 230 thereby causing the plunger to move 170 to decrease the volume of the metering chamber 130. After actuation and aerosolization, the spring 240 returns the stem 235 to the position shown in FIG. 8 and as the pressure in the metering chamber 130 and in the reservoir equilibrate, the biasing member 230 returns the plunger to its extended position so that the aerosolization device 100 is again armed for actuation.

Other pressurizer 165 versions may also be used with the stem actuator. For example, FIG. 9 shows a specific version of a metering valve 125 comprising a pressurizer 165 having a flexible wall 180 of the type described above in connection with the version of FIGS. 3A and 3B and with the version of FIGS. 6A and 6B. The flexible wall 180 is shown in its extended position in FIG. 9 where it defines the volume of the metering chamber 130. During actuation of the aerosolization device 100 by moving the stem 235 as described above, the flexible wall 180 collapses under the force of the pressure in the reservoir 110 to reduce the volume of the metering chamber 130. A biasing mechanism, such as a leaf spring, may be provided to cause the flexible wall 180 to move to the extended position shown in FIG. 9.

In another exemplary version, FIG. 10 shows a version of a metering valve 125 having a pressurizer 165 that introduces pressurized gas into the metering chamber 130 during actuation, as described above in connection with FIGS. 7A and 7B. The conduit 205 that extends to the gaseous portion 120 in the container 105 is connected to and extends partially through the stem 235. The third valving mechanism 195 is operated by movement of the stem 235. The third valving mechanism 195 comprises a lower end 251 of the conduit 205 and a wall 255 of the metering chamber 130. In FIG. 10, the third valving mechanism 195 is in its closed position which is provided by the end 251 of the conduit 205 being blocked by the wall 255 of the metering chamber 130. As the stem 235 moves upward, the end 205 also moves upward until it reaches a portion 260 of the metering chamber where the end 250 does not contact the wall 255. At this position, the metering chamber 130 is in communication with the gaseous portion 120 and the pressurized gas is introduced into the metering chamber 130 to increase the pressure therein. In one version, the portion 260 is sufficiently small that the third valving mechanism 195 is open only for a period of the actuation process so that a burst of pressurized gas is introduced.

FIG. 11 shows another version of an aerosolization device 100 having a metering valve 125 with a pressurizer 165 that comprises a bi-stable member 280. For example, the bi-stable member 280 may be in the form of a bi-stable dome that is stable in at least two positions, such as the dome configuration shown in FIG. 11 in solid lines and in an inverted configuration 285 shown in broken lines. In this version, the bi-stable member 280 assumes the dome configuration when the pressure on the interior 290 is substantially the same as the pressure on the exterior 295. The bi-stable member then moves to the inverted configuration 285 when the exterior pressure exceeds the interior pressure. FIG. 11 shows the metering valve in the filling position. In this position, the pharmaceutical formulation within the reservoir 110 of the container 105 passes through an opening 305 and into the metering chamber volume 130 that includes the interior 290 of the bi-stable member 280. When the metering valve 125 is actuated by moving the valve stem 235 upwardly, the top of the stem 310 contacts a sealing member 315 to close the metering chamber 130 from the reservoir 110. As the stem 235 continues to move upwardly, an opening 320 into the metering chamber 130 and the opening 250 into the interior 150 of the expansion chamber 145 are in communication so that the metered volume of the pharmaceutical formulation may be aerosolized, as discussed above. During the aerosolization process, the pressure is lowered in the metering chamber 130. This causes the bi-stable member 280 to invert to the inverted position 285, thereby decreasing the volume of the metering chamber 130 and increasing the pressure therein when compared to metering chamber that maintains a constant volume. For the sake of clarity, the return spring 240 that returns the stem 235 to its filling position is not shown in the figure.

FIG. 12 shows data obtained from experiments performed with the version of the aerosolization device shown in FIG. 8. The graph shows expansion chamber pressure using an HFA propellant. Two tests were performed with the metering chamber volume held constant. The resulting curves are shown at 370. In addition, four tests were performed with the volume of the metering chamber being reduced by the movement of the plunger during actuation. These variable volume curves are shown at 375. As can be seen, the pressurizer 165 of the present invention allows for a longer aerosolization period and correspondingly allows for a larger amount of the pharmaceutical formulation to be aerosolized.

The reservoir 110 may be in a canister in which a pharmaceutical formulation is stored in or with a propellant, such as a hydrofluoroalkane, as discussed in U.S. Pat. Nos. 5,225,183; 5,681,545; 5,683,677; 5,474,759; 5,508,023; 6,309,623 and in U.S. Pat. No. 5,655,520 all of which are incorporated herein by reference in their entireties. Propellant based metered dose inhalers may employ a dry powdered pharmaceutical formulation which is suspended or dissolved in a liquefied gas propellant. The pharmaceutical formulation may further comprise one or more excipients or surfactants to aid in the suspension and/or in the solubility, as discussed in the above-listed patents. After actuation, the propellant evaporates almost immediately leaving a fine dry powder.

In a preferred version, the invention provides a system and method for aerosolizing a pharmaceutical formulation and delivering the pharmaceutical formulation to the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperatures (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), both of which are incorporated herein by reference in their entireties.

The pharmaceutical formulation may also be treated so that it has high stability. Several attempts have dealt with improving suspension stability by increasing the solubility of surface-active agents in the HFA propellants. To this end U.S. Pat. No. 5,118,494, WO 91/11173 and WO 92/00107 disclose the use of HFA soluble fluorinated surfactants to improve suspension stability. Mixtures of HFA propellants with other perfluorinated cosolvents have also been disclosed as in WO 91/04011. Other attempts at stabilization involved the inclusion of nonfluorinated surfactants. In this respect, U.S. Pat. No. 5,492,688 discloses that some hydrophilic surfactants (with a hydrophilic/lipophilic balance greater than or equal to 9.6) have sufficient solubility in HFAs to stabilize medicament suspensions. Increases in the solubility of conventional nonfluorinated MDI surfactants (e.g. oleic acid, lecithin) can also reportedly be achieved with the use of co-solvents such as alcohols, as set forth in U.S. Pat. Nos. 5,683,677 and 5,605,674, as well as in WO 95/17195. Unfortunately, as with the prior art cosolvent systems previously discussed, merely increasing the repulsion between particles has not proved to be a very effective stabilizing mechanism in nonaqueous dispersions, such as MDI preparations. All of the aforementioned references being incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 μm MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

In one particular example, the pharmaceutical formulation comprises insulin. Example of suitable suspension or solution insulin formulations can be found in U.S. Pat. Nos. 5,006,343; 5,364,838; 6,432,383; 6,540,982, all of which are incorporated herein by reference in their entireties. A particularly useful formulation of insulin comprises insulin in a phospholipid matrix, as disclosed in U.S. Pat. No. 6,433,040 and suspended in an HFA propellant as described in U.S. Pat. No. 6,309,623, both of which are incorporated herein by reference in their entireties. The advantage of aerosolizing the insulin formulations using the aerosolization device 100 of the present invention is that large and/or uniform doses can be generated that are not possible to generate in conventional meter dose inhalers. For example, at least a 2 mg dose of insulin can be administered using the above formulations in combination with an aerosolization device 100 of the present invention. In other versions, at least 3 mg and at least 5 mg of insulin can be aerosolized for delivery to a patient in need of insulin.

A capture chamber may be provided in certain applications. Suitable capture chambers are disclosed in U.S. Pat. Nos. 5,458,135; 5,740,794; 6,257,233; and U.S. Pat. No. 4,534,343, all of which are incorporated herein by reference in their entireties. The capture chamber may be useful when a user is unable to coordinate his or her inhalation with the actuation of the aerosolization device 100 or when the dose is sufficiently large that it is aerosolized in a manner than causes a stream of medicament to impact the back of a user's throat during use.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the relative positions of the elements in the aerosolization device may be changed, and flexible parts may be replaced by more rigid parts that are hinged, or otherwise movable, to mimic the action of the flexible part. In addition, the passageways need not necessarily be substantially linear, as shown in the drawings, but may be curved or angled, for example. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. An aerosolization apparatus comprising:
a container containing a pharmaceutical formulation, the pharmaceutical formulation comprising an active agent and a propellant;
a metering chamber in communication with the container, the metering chamber adapted to hold a metered amount of the pharmaceutical formulation;
a valve to allow the metered amount of the pharmaceutical formulation to be released from the metering chamber when the valve is actuated; and
a pressurizer that applies pressure to the pharmaceutical formulation in the metering chamber while the pharmaceutical formulation is being released from the metering chamber,
wherein the metering chamber is adapted to contain a volume of the pharmaceutical formulation of at least 150 μl prior to actuation of the valve, and wherein the metering chamber is sized so that at least 2 mg of the active agent is be aerosolized for delivery to a user during inhalation.

2. An aerosolization apparatus according to claim 1 wherein the pressurizer changes the volume of the metering chamber.

3. An aerosolization apparatus according to claim 1 wherein the pressurizer decreases the volume of the metering chamber.

4. An aerosolization apparatus according to claim 1 wherein the pressurizer changes the volume of the metering chamber and wherein the aerosolization apparatus further comprises a mechanism for returning the metering chamber to its original volume following actuation.

5. An aerosolization apparatus according to claim 1 wherein the metering chamber is sized so that at least 3 mg of the active agent is be aerosolized for delivery to a user during inhalation.

6. An aerosolization apparatus according to claim 1 wherein the metering chamber is sized so that at least 5 mg of the active agent is be aerosolized for delivery to a user during inhalation.

7. An aerosolization apparatus according to claim 1 wherein the metering chamber is adapted to contain a volume of the pharmaceutical formulation of at least 50 μl prior to actuation of the valve.

8. An aerosolization apparatus according to claim 1 wherein the metering chamber is adapted to contain a volume of the pharmaceutical formulation of at least 300 μl prior to actuation of the valve.

9. An aerosolization apparatus according to claim 1 wherein the pressurizer is arranged so that at least 50% of the aerosol particles generated have a diametric size of from 0.1 μm to 10 μm.

10. An aerosolization apparatus according to claim 1 wherein the pressurizer is arranged so that at least 80% of the aerosol particles generated have a diametric size of from 0.1 μm to 10 μm.

11. An aerosolization apparatus according to claim 1 wherein the pressurizer comprises a plunger that is capable of changing the volume of the metering chamber.

12. An aerosolization apparatus according to claim 1 wherein the pressurizer comprises a plunger that is capable of changing the volume of the metering chamber, wherein the plunger is adapted to be pressurized by the pressure of the pharmaceutical formulation within the container.

13. An aerosolization apparatus according to claim 1 wherein the pressurizer comprises a flexible wall of the metering chamber.

14. An aerosolization apparatus according to claim 1 wherein the pressurizer comprises a flexible wall of the metering chamber, wherein the flexible wall is adapted to be pressurized by the pressure of the pharmaceutical formulation within the container.

15. An aerosolization apparatus according to claim 1 wherein the pressurizer comprises a source of pressurized gas.

16. An aerosolization apparatus according to claim 1 wherein the pressurizer comprises a source of pressurized gas, wherein the source of pressurized gas is within the container.

17. An aerosolization apparatus according to claim 1 wherein the pressurizer comprises a bi-stable member movable between a first position and a second position and wherein the pressure within the metering chamber is increased when the bi-stable member moves to the second position.

18. An aerosolization apparatus according to claim 17 wherein the bi-stable member comprises a bi-stable dome.

19. An aerosolization apparatus according to claim 17 wherein the bi-stable member comprises an interior surface in communication with the metering chamber and an exterior surface in communication with the interior of the container.

20. An aerosolization apparatus comprising:
a container containing a pharmaceutical formulation, the pharmaceutical formulation comprising an active agent and a propellant;
a metering chamber in communication with the container, the metering chamber having a metering volume of at least 150 μl and being adapted to hold a metered amount of the pharmaceutical formulation;
a valve to allow the metered amount of the pharmaceutical formulation to be released from the metering chamber when the valve is actuated; and
a pressurizer that applies pressure to the pharmaceutical formulation in the metering chamber while the pharmaceutical formulation is being released from the metering chamber.

21. An aerosolization apparatus according to claim 20 wherein the pressurizer changes the volume of the metering chamber.

22. An aerosolization apparatus according to claim 20 wherein the pressurizer changes the volume of the metering chamber and wherein the aerosolization apparatus further comprises a mechanism for returning the metering chamber to its original volume following actuation.

23. An aerosolization apparatus according to claim 20 wherein the pressurizer is arranged so that at least 50% of the aerosol particles generated have a diametric size of from 0.1 μm to 10 μm.

24. An aerosolization apparatus according to claim 20 wherein the pressurizer comprises a plunger that is capable of changing the volume of the metering chamber, wherein the plunger is adapted to be pressurized by the pressure of the pharmaceutical formulation within the container.

25. An aerosolization apparatus according to claim 20 wherein the pressurizer comprises a flexible wall of the metering chamber, wherein the flexible wall is adapted to be pressurized by the pressure of the pharmaceutical formulation within the container.

26. An aerosolization apparatus according to claim 20 wherein the pressurizer comprises a source of pressurized gas, wherein the source of pressurized gas is within the container.

27. An aerosolization apparatus according to claim 20 wherein the pressurizer comprises a bi-stable member movable between a first position and a second position and wherein the pressure within the metering chamber is increased when the bi-stable member moves to the second position.

28. An aerosolization apparatus comprising:
a container containing a pharmaceutical formulation, the pharmaceutical formulation comprising insulin and a propellant;
a metering chamber in communication with the container, the metering chamber adapted to hold a metered amount of the pharmaceutical formulation;
a valve to allow the metered amount of the pharmaceutical formulation to be released from the container when the valve is actuated; and
a pressurizer that applies pressure to the pharmaceutical formulation in the metering chamber while the pharmaceutical formulation is released from the metering chamber,
wherein the metering chamber is sized so that more than about 5 mg of insulin is aerosolized for delivery to a user during inhalation.

29. An aerosolization apparatus according to claim 28 wherein the pressurizer comprises a plunger that is capable of changing the volume of the metering chamber, wherein the plunger is adapted to be pressurized by the pressure of the pharmaceutical formulation within the container.

30. An aerosolization apparatus according to claim 28 herein the pressurizer comprises a bi-stable member movable between a first position and a second position and wherein the pressure within the metering chamber is increased when the bi-stable member moves to the second position.

31. A method of aerosolizing a pharmaceutical formulation, the method comprising:
containing a pharmaceutical formulation in a container, the pharmaceutical formulation comprising an active agent and a propellant;
metering an amount of the pharmaceutical formulation in a metering chamber in communication with the container, wherein the metered amount is at least 150 μl;
releasing the pharmaceutical formulation from the metering chamber when a valve is actuated; and
applying pressure within the metering chamber during the release of the pharmaceutical formulation,
wherein at least 2 mg of the active agent is be aerosolized for delivery to a user during inhalation.

32. A method according to claim 31 wherein the pressure is added to the metering chamber by decreasing the volume of the metering chamber.

33. A method according to claim 31 wherein at least 3 mg of the active agent is aerosolized for delivery to a user during inhalation.

34. A method according to claim 31 wherein at least 5 mg of the active agent is aerosolized for delivery to a user during inhalation.

35. A method according to claim 31 wherein at least 50% of the aerosol particles generated have a diametric size of from 0.1 μm to 10 μm.

36. A method according to claim 31 wherein at least 80% of the aerosol particles generated have a diametric size of from 0.1 μm to 10 μm.

37. A method according to claim 31 wherein the pressure is applied by a plunger.

38. A method according to claim 31 wherein the pressure is applied by a plunger, wherein the plunger is adapted to be pressurized by the pressure of the pharmaceutical formulation within the container.

39. A method according to claim 31 wherein the pressure is applied by a flexible wall of the metering chamber, wherein the flexible wall is pressurized by the pressure of the pharmaceutical formulation within the container.

40. A method according to claim 31 wherein the pressure is applied from a source of pressurized gas.

41. A method according to claim 31 wherein the pressure is applied by a bi-stable member movable between a first position and a second position and wherein the pressure within the metering chamber is increased when the bi-stable member moves to the second position.

42. A method of aerosolizing an insulin formulation, the method comprising:

containing a pharmaceutical formulation in a container, the pharmaceutical formulation comprising insulin and a propellant;

metering an amount of the pharmaceutical formulation in a metering chamber in communication with the container;

releasing the pharmaceutical formulation from the metering chamber when a valve is actuated; and applying pressure within the metering chamber during the release of the pharmaceutical formulation, wherein at least 5 mg of insulin is aerosolized for delivery to a user.

43. A method according to claim 42 wherein at least 2 mg of insulin is aerosolized for delivery to a user.

44. A method according to claim 42 wherein at least 3 mg of insulin is aerosolized for delivery to a user.

45. A method according to claim 42 wherein the pressure is applied by a plunger, wherein the plunger is adapted to be pressurized by the pressure of the pharmaceutical formulation within the container.

46. A method according to claim 42 wherein the pressure is applied by a flexible wall of the metering chamber, wherein the flexible wall is pressurized by the pressure of the pharmaceutical formulation within the container.

47. A method according to claim 42 wherein the pressure is applied from a source of pressurized gas.

48. A method according to claim 42 wherein the pressure is applied by a bi-stable member movable between a first position and a second position and wherein the pressure within the metering chamber is increased when the bi-stable member moves to the second position.

* * * * *